US00PP30560P2

(12) United States Plant Patent
Klemm et al.

(10) Patent No.: US PP30,560 P2
(45) Date of Patent: Jun. 4, 2019

(54) ***OSTEOSPERMUM*PLANT NAMED 'KLEOE17333'**

(50) Latin Name: *Osteospermum ecklonis*
Varietal Denomination: KLEOE17333

(71) Applicant: Klemm+Sohn GmbH & Co. KG, Stuttgart (DE)

(72) Inventors: Nils Klemm, Stuttgart (DE); Maike Boxriker, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/998,064

(22) Filed: Jun. 21, 2018

(51) Int. Cl.
*A01H 5/02* (2018.01)

(52) U.S. Cl.
USPC ..... Plt./360

(58) Field of Classification Search
USPC ..... Plt./360
See application file for complete search history.

*Primary Examiner* — Annette H Para
(74) *Attorney, Agent, or Firm* — Barbara Campbell; Bethany R. Roahrig; Cochran Freund & Young LLC

(57) ABSTRACT

A new *Osteospermum* plant particularly distinguished by red-purple flowers with greyed-white eyes and an upright growth habit, is disclosed.

1 Drawing Sheet

Genus and species: *Osteospermum ecklonis.*
Variety denomination: 'KLEOE17333'.

BACKGROUND OF THE NEW PLANT

The present invention comprises a new and distinct variety of *Osteospermum*, botanically known as *Osteospermum ecklonis*, and hereinafter referred to by the variety name 'KLEOE17333'. 'KLEOE17333' originated from a cross-pollination conducted in May to October 2013 in Nairobi, Kenya between the female *Osteospermum* variety SPRINGSTAR 'Magenta' (patent status unknown), and the proprietary male *Osteospermum* variety 'KLOEO14215' (U.S. Plant Pat. No. 26,694).

The seeds from the cross were sown and plants were grown in a greenhouse for evaluation, where an individual plant designated 'KLEOE17333' was selected from the group of plants in May 2014 in Stuttgart, Germany. In October 2014 in Stuttgart, Germany, 'KLEOE17333' was first vegetatively propagated by vegetative terminal cuttings. 'KLEOE17333' was found to reproduce true to type in successive generations of asexual propagation via vegetative terminal cuttings.

SUMMARY

The following are the most outstanding and distinguishing characteristics of this new variety when grown under normal horticultural practices in Stuttgart, Germany.

1. Red-purple flowers with greyed-white eyes; and
2. An upright growth habit.

DESCRIPTION OF THE PHOTOGRAPH

This new *Osteospermum* plant is illustrated by the accompanying photograph which shows the plant's overall plant habit including form, foliage, and flowers. The photograph is of a 10-week-old plant grown in a greenhouse in Stuttgart, Germany in April 2016. The colors shown are as true as can be reasonably obtained by conventional photographic procedures.

DESCRIPTION OF THE NEW VARIETY

The following detailed descriptions set forth the distinctive characteristics of 'KLEOE17333'. The data which define these characteristics were collected on plants after 11 weeks (at the time of flowering) in Stuttgart, Germany in April 2018. The plants were treated with CYCOCEL three times. Color references are to The R.H.S. Colour Chart of The Royal Horticultural Society of London (R.H.S.), 5$^{th}$ edition (2007).

Classification:
- *Family.*—Asteraceae.
- *Botanical.*—*Osteospermum ecklonis.*
- *Common.*—*Osteospermum.*
- *Designation.*—'KLEOE17333'.

Parentage:
- *Female parent.*—The female *Osteospermum* variety SPRINGSTAR 'Magenta' (patent status unknown).
- *Male parent.*—The proprietary male *Osteospermum* variety 'KLOEO14215' (U.S. Plant Pat. No. 26,694).

Plant:
- *Form and habit.*—Herbaceous perennial but usually cultivated as an annual; not frost resistant.
- *Growth habit.*—Upright.
- *Branching habit.*—Normal.
- *Height (from top of soil, including inflorescence).*—8.0 cm.
- *Width (including inflorescences).*—19.0 cm.
- *Propagation.*—Vegetative terminal cuttings.
- *Time to produce a finished flowering plant.*—About 9 weeks.
- *Time to initiate and develop roots.*—3 to 4 weeks.
- *Root description.*—Light tan in color, fine.

Stems:
- *Total number of branches per plant (calculated at the base of the plant).*—4.

*Length.*—11.0 cm.
*Diameter.*—0.3 cm.
*Internode length.*—1.0 cm.
*Color.*—RHS 144A (Yellow-green).
*Texture.*—Smooth, but with fine hairs.
*Anthocyanin.*—Absent.

Leaves:
*Arrangement.*—Alternate.
*Shape.*—Obovate.
*Apex.*—Acute.
*Base.*—Acute.
*Immature color.*—Upper surface: RHS N137A (Green). Lower surface: RHS 137B (Green).
*Mature color.*—Upper surface: RHS 137B (Green). Lower surface: RHS 137C (Green).
*Length.*—3.5 cm.
*Width.*—1.1 cm.
*Texture.*—Upper surface: Leathery and shiny. Lower surface: Leathery and shiny, and covered with some fine hairs.
*Petioles.*—Absent.
*Venation pattern.*—Pinnate.
*Venation color* (*both upper and lower surfaces*).—RHS 145A (Yellow-green).

Flower buds:
*Shape.*—Round-ovoid.
*Apex.*—Obtuse.
*Base.*—Acute.
*Margin.*—Entire.
*Texture.*—Smooth with fine hairs.
*Length.*—1.5 cm.
*Diameter.*—1.2 cm.
*Color* (*at tight bud just before the ray florets unfold*).—RHS 143A (Green).

Inflorescence:
*Type.*—Composite, single.
*Blooming habit.*—Upright.
*Quantity of inflorescences per plant.*—4.
*Lastingness of the inflorescences on the plant.*—10 to 15 days.
*Fragrance.*—Present.
*Inflorescence diameter.*—6.5 cm.
*Inflorescence depth.*—1.5 cm.

Disc floret:
*Quantity per inflorescence.*—About 30.
*Shape.*—Tubular.
*Tube color.*—Closed: RHS NN155 (White). Mature: RHS 156D (Greyed-white).
*Length.*—0.5 cm.
*Diameter* (*at apex*).—0.1 cm.
*Apex.*—Acute.
*Apex color.*—RHS N187B (Greyed-purple).
*Base.*—Acute.
*Base color.*—RHS 156D (Greyed-white).
*Margin.*—Entire.

Ray floret:
*Quantity per inflorescence.*—24.
*Shape.*—Oblanceolate.
*Color.*—Upper surface: RHS 71A (Red-purple). Lower surface: RHS 70B (Red-purple).
*Length.*—3.0 cm.
*Width.*—0.7 cm.
*Apex.*—Acute.
*Base.*—Acute.
*Margin.*—Entire.
*Texture.*—Upper surface: Smooth. Lower surface: Smooth, shiny.

Peduncle:
*Length.*—5.0 cm.
*Diameter.*—0.2 cm.
*Texture.*—Smooth with hairs.
*Color.*—RHS 145A (Yellow-green).

Phyllaries:
*Arrangement.*—Single.
*Observed quantity per flower.*—24.
*Shape.*—Lanceolate.
*Apex.*—Acute.
*Base.*—Obtuse.
*Margin.*—Entire.
*Length.*—1.1 cm.
*Width.*—0.2 cm.
*Texture.*—Upper surface: Smooth with fine hairs. Lower surface: Smooth.
*Color.*—Upper surface: RHS 143A (Green). Lower surface: RHS 144A (Yellow-green).

Reproductive organs:
*Androecium.*—Location: On disc and ray florets. Stamens: Shape: Filamentous. Quantity: Numerous. Filament length: 0.4 cm. Filament diameter: Greater than 0.1 cm. Anther: Shape: Lanceolate. Color: RHS N77A (Purple). Length: Greater than 0.1 cm. Diameter: Greater than 0.1 cm. Pollen: Color: RHS 14A (Yellow-orange). Amount: Abundant.
*Gynoecium.*—Location: On the phyllary. Pistils: Number: Numerous. Length: 0.5 cm. Diameter: Greater than 0.1 cm. Stigma: Color: RHS N77A (Purple). Shape: Tapering filamentous and split in two parts. Length: 0.2 cm. Diameter: Greater than 0.1 cm. Style: Color: RHS 156C (Greyed-white). Length: 0.3 cm. Diameter: Greater than 0.1 cm.

Fruit and seed set: None observed.

Disease and pest/insect resistance: No disease and pest/insect resistance observed.

COMPARISON WITH PARENTAL LINES AND KNOWN VARIETY

'KLEOE17333' is a distinct variety of *Osteospermum* and is distinguished from its parents as described in Table 1.

TABLE 1

Comparison with Parental Lines

| Characteristic | 'KLEOE17333' | Female Parent SPRINGSTAR 'Magenta' | Male Parent 'KLEOE14215' |
|---|---|---|---|
| Flower Color | Red-purple | Purple | White |
| Habit | Upright | Upright | Spreading |

'KLEOE17333' is most similar to the commercial *Osteospermum* variety 'KLEO9156' (unpatented). Differences between the varieties are described in Table 2.

TABLE 2

Comparison with Similar Variety

| Characteristic | 'KLEOE17333' | 'KLEO9156' |
|---|---|---|
| Flower color | Red-purple | Cream |

We claim:

1. A new and distinct variety of *Osteospermum* plant designated 'KLEOE17333' as illustrated and described herein.

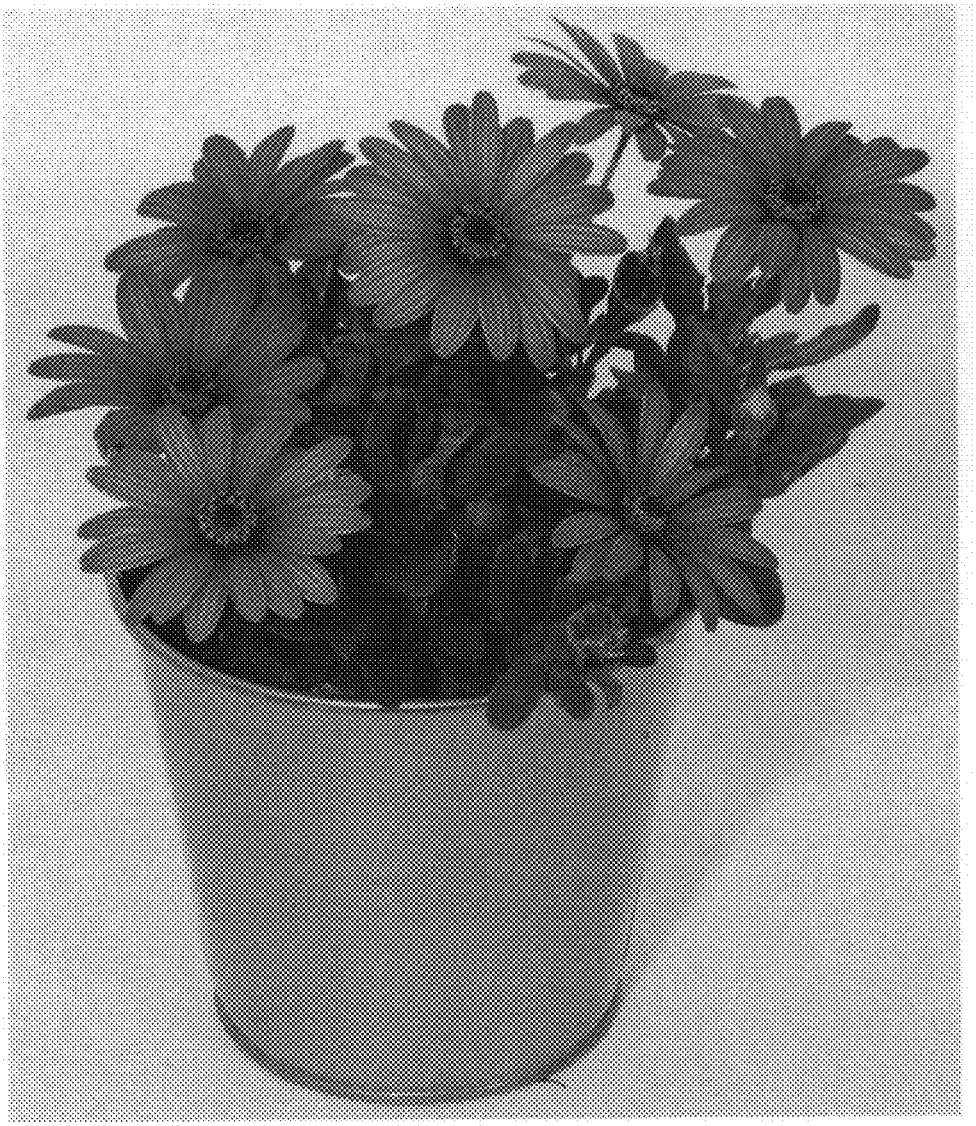

* * * * *